(12) United States Patent
Takahashi et al.

(10) Patent No.: US 8,709,780 B2
(45) Date of Patent: Apr. 29, 2014

(54) METHOD FOR PRODUCING PURIFIED INFLUENZA VIRUS ANTIGEN

(75) Inventors: Koichi Takahashi, Machida (JP); Kazuaki Maeda, Machida (JP); Noriyuki Izutani, Machida (JP); Shinichi Yanagi, Machida (JP); Yukiko Nakashima, Machida (JP)

(73) Assignee: Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/121,625

(22) PCT Filed: Sep. 29, 2009

(86) PCT No.: PCT/JP2009/066893
§ 371 (c)(1),
(2), (4) Date: Mar. 29, 2011

(87) PCT Pub. No.: WO2010/038719
PCT Pub. Date: Apr. 8, 2010

(65) Prior Publication Data
US 2011/0182940 A1 Jul. 28, 2011

(30) Foreign Application Priority Data
Sep. 30, 2008 (JP) .................................. 2008-253742

(51) Int. Cl.
*C12N 7/02* (2006.01)
*A61K 39/145* (2006.01)

(52) U.S. Cl.
USPC ........................................ 435/239; 424/206.1

(58) Field of Classification Search
None
See application file for complete search history.

(56) References Cited

U.S. PATENT DOCUMENTS

| | | | |
|---|---|---|---|
| 4,327,182 A | 4/1982 | Benedictus | |
| 6,165,774 A | 12/2000 | Cates et al. | |
| 6,221,365 B1 | 4/2001 | Jones | |

FOREIGN PATENT DOCUMENTS

| | | |
|---|---|---|
| GB | 2 348 886 A | 10/2000 |
| JP | 7-258291 A | 10/1995 |
| JP | 07-258291 A | 10/1995 |
| JP | 9-169794 A | 6/1997 |
| JP | 11-513372 A | 11/1999 |
| JP | 2000-262280 A | 9/2000 |
| WO | WO 2007/089753 A2 | 8/2007 |

OTHER PUBLICATIONS

Wang K, Holtz KM, Anderson K, Chubet R, Mahmoud W, Cox MM. Expression and purification of an influenza hemagglutinin—one step closer to a recombinant protein-based influenza vaccine.Vaccine. Mar. 15, 2006;24(12):2176-85. Epub Nov. 10, 2005.*
Pickering et al. Influenza virus pyrogenicity: central role of structural orientation of virion components and involvement of viral lipid and glycoproteins. J Gen Virol. Jun. 1992;73 ( Pt 6):1345-54.*
Avalos RT et al. Association of influenza virus NP and M1 proteins with cellular cytoskeletal elements in influenza virus-infected cells. J Virol. Apr. 1997;71(4):2947-58.*
Abstract of JP 2001-524803 published Dec. 4, 2001.
International Preliminary Report on Patentability and Written Opinion issued May 10, 2011, in PCT International Application No. PCT/JP2009/066893.
International Search Report issued Dec. 22, 2009, in PCT International Application No. PCT/JP2009/066893.
Wang et al., "Expression and purification of an influenza hemagglutinin—one step closer to a recombinant protein-based influenza vaccine," Vaccine (2006) vol. 24, pp. 2176-2185.
European Search Report issued in European Patent Application No. 09817751.2 on Dec. 3, 2012.

\* cited by examiner

*Primary Examiner* — Mary E Mosher
*Assistant Examiner* — Nick Zou
(74) *Attorney, Agent, or Firm* — Birch, Stewart, Kolasch & Birch, LLP

(57) ABSTRACT

The present invention aims to provide a method which enables efficient removal of impurities such as the host proteins from an influenza virus culture liquid by a simple operation, allowing separation and purification of an influenza virus antigen. The method of the present invention for producing a purified influenza virus antigen comprises the step of treating a sample containing an influenza virus with a surfactant, the step of bringing the sample after the treatment into contact with hydroxyapatite in the presence of the surfactant, and the step of recovering a hydroxyapatite-non-adsorbed fraction.

17 Claims, 13 Drawing Sheets

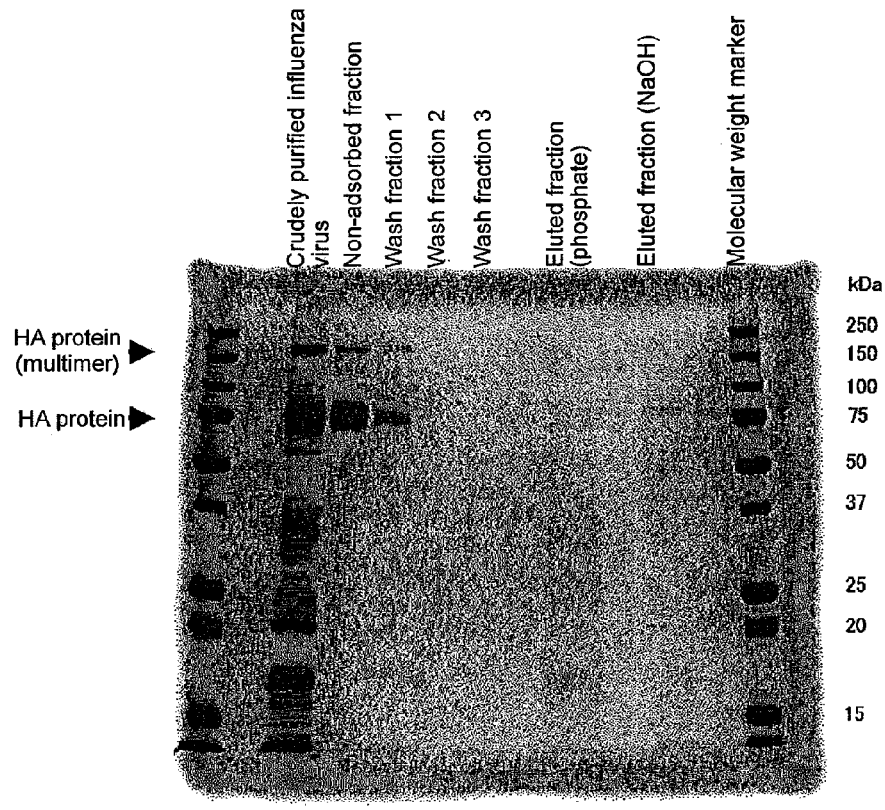

Fig.6

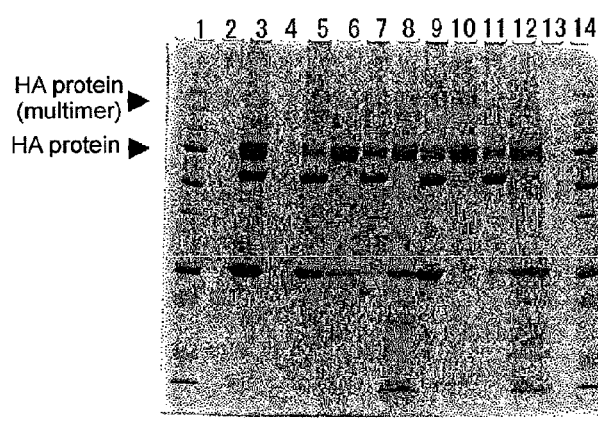

1. Molecular weight marker
2. Blank
3. Crudely purified influenza virus liquid
4. Blank
5. Triton X-100 treatment, precipitate obtained by centrifugation
6. Triton X-100 treatment, supernatant obtained by centrifugation
7. Tween-CTAB treatment, precipitate obtained by centrifugation
8. Tween-CTAB treatment, supernatant obtained by centrifugation
9. CHAPS treatment, precipitate obtained by centrifugation
10. CHAPS treatment, supernatant obtained by centrifugation
11. DOC treatment, precipitate obtained by centrifugation
12. DOC treatment, supernatant obtained by centrifugation
13. Blank
14. Molecular weight marker

Fig.7

METHOD FOR PRODUCING PURIFIED INFLUENZA VIRUS ANTIGEN

TECHNICAL FIELD

The present invention relates to a method for producing a purified influenza virus antigen.

BACKGROUND ART

Influenza virus is an RNA virus belonging to Orthomyxoviridae, and known to be divided into the type A, type B and type C.

Influenza virus has an envelope having the lipid bilayer membrane structure. The inner layer of the envelope is mainly composed of matrix protein, and RNP, which is a complex between RNA and protein. On the outer layer, influenza NA protein (neuraminidase) and influenza HA protein (hemagglutinin) (hereinafter referred to as "NA protein" and "HA protein", respectively), which are the so called surface proteins, exist as projections.

Viruses belonging to the same type are further classified into plural subtypes and strains based on the antigenicities of HA protein and NA protein, respectively. As influenza vaccines, those wherein an adjuvant, antiseptic and/or the like were added to a stock solution containing NA protein and HA protein are commonly used.

Influenza virus to be used for influenza vaccines is cultured mainly in embryonated chicken eggs. Further, in recent years, methods for culturing influenza virus by animal cell culture systems have been established.

Since, in general, influenza virus obtained by these methods does not exist solely but exists together with cultured cells, impure proteins and the like, the influenza virus needs to be separated from culture liquid or the like. Separation and purification of influenza virus are carried out by ultracentrifugation, ultrafiltration, density gradient centrifugation and/or the like.

However, even in the influenza virus separated and purified by these methods, impure proteins derived from the host are often observed. In cases where an influenza vaccine containing such impure proteins is inoculated, side effects such as anaphylactic shock or Guillain-Barre syndrome may occur, so that further purification is required.

Known examples of the method for producing an influenza antigen include a method wherein a gene for producing a protein antigen contained in an influenza virus is incorporated into an animal cell or insect cell.

As an example of the method for purifying influenza virus, a method wherein influenza virus or an influenza virus antigen is purified using hydroxyapatite is already known (Patent Document 1). The method according to Patent Document 1 comprises a step of adsorption of virus or a virus antigen to hydroxyapatite and a step of elution by an eluent. However, since various strains of influenza virus exist and the sequences of HA protein and NA protein vary among the strains, the elution position may vary among the influenza virus strains under the constant elution conditions, leading to different purities among the strains. Therefore, it is necessary to strictly control the conditions of elution of the adsorbed protein for each influenza virus strain, which is very complicated in view of production.

In Patent Document 2, a method for purifying a recombinant HA protein using a carrier to which a sialo-sugar-chain-containing compound was immobilized is disclosed, which method uses the property of HA protein to specifically adsorb to specific sugar chains. However, in this method, there are problems such as requirement of much labor in preparation of the carrier to which a sialo-sugar-chain-containing compound was immobilized, and probability of difficulty in the purification in cases where a large mutation occurred in the HA protein of the influenza virus strain.

In Non-patent Document 1, a method for preparation of HA protein, wherein a gene having information to allow production of HA protein of influenza virus is incorporated into animal cells (insect cells) by gene recombination to produce recombinant cells, which are then cultured, thereby producing HA protein, is described. This method requires thorough removal of impure proteins derived from the recombinant cells.

PRIOR ART DOCUMENTS

Patent Documents

[Patent Document 1] JP 2000-262280 A
[Patent Document 2] JP 3476242 B

Non-Patent Document

[Non-patent Document 1] Vaccine 24 (2006) 2176-2185 Expression and purification of an influenza hemagglutinin—one step closer to a recombinant protein-based influenza vaccine.

DISCLOSURE OF THE INVENTION

Problems to be Solved by the Invention

The present invention aims to provide a method that allows simple and efficient removal of impurities such as the host proteins from culture liquid of influenza virus containing an influenza virus antigen or from culture liquid of recombinant cells to which a gene for producing an influenza antigen was incorporated, which method thereby enables separation and purification of the influenza antigen.

Means for Solving the Problems

The present inventors intensively studied to discover that, by crudely purifying a sample containing an influenza antigen such as culture liquid of influenza virus cultured by the chicken egg culture system or the animal cell culture system and treating the resulting product with a surfactant, followed by carrying out centrifugation and/or filtration separation as appropriate and bringing the resultant into contact with hydroxyapatite in the presence of a surfactant, impurities in the culture liquid are adsorbed to the hydroxyapatite and an influenza antigen such as HA protein can be obtained in the non-adsorbed fraction at high purity, thereby completing the present invention.

That is, the present invention provides a method for producing a purified influenza virus antigen, the method comprising the steps of treating a sample containing an influenza virus antigen with a surfactant; bringing the sample after the treatment into contact with hydroxyapatite in the presence of the surfactant; and recovering the fraction not adsorbed by the hydroxyapatite. The present invention also provides a method for producing an influenza vaccine, which method comprises producing a purified influenza virus antigen by the above-described method of the present invention. Further, the present invention provides an influenza vaccine containing a purified influenza virus antigen produced by the above-described method of the present invention, and a prefilled kit produced by filling the influenza vaccine into a container with which inoculation is possible. Further, the present invention provides a diagnostic reagent for influenza containing a purified influenza virus antigen produced by the above-described method of the present invention. Further, the present invention provides a diagnostic kit for influenza containing a purified influenza virus antigen produced by the above-described method of the present invention.

Unless otherwise specified, in the present description, the concentration and the pH value of each component in a sample indicate the concentration and pH value immediately before bringing the sample into contact with hydroxyapatite. Further, unless otherwise specified, the unit of concentration % is w/v %.

Effect of the Invention

By the present invention, an antigen protein such as HA protein can be prepared by a simple operation from an influenza virus antigen-containing sample in which various impurities are contained, to prepare a purified influenza virus antigen at high purity, and the resulting antigen can be obtained at high recovery. By the method of the present invention, a purified influenza virus antigen which has a lower risk of serious side effects such as anaphylactic shock, and which is useful as a vaccine and highly safe and effective can be obtained economically.

BRIEF DESCRIPTION OF THE DRAWINGS

FIG. 6 is a diagram showing the result of SDS-PAGE (non-reducing, CBB staining) of each of the fractions obtained in Example 4.

FIG. 7 is a diagram showing the result of SDS-PAGE (non-reducing, CBB staining) of each of the supernatant and precipitate fractions obtained in Example 5.

BEST MODE FOR CARRYING OUT THE INVENTION

Figure 1:
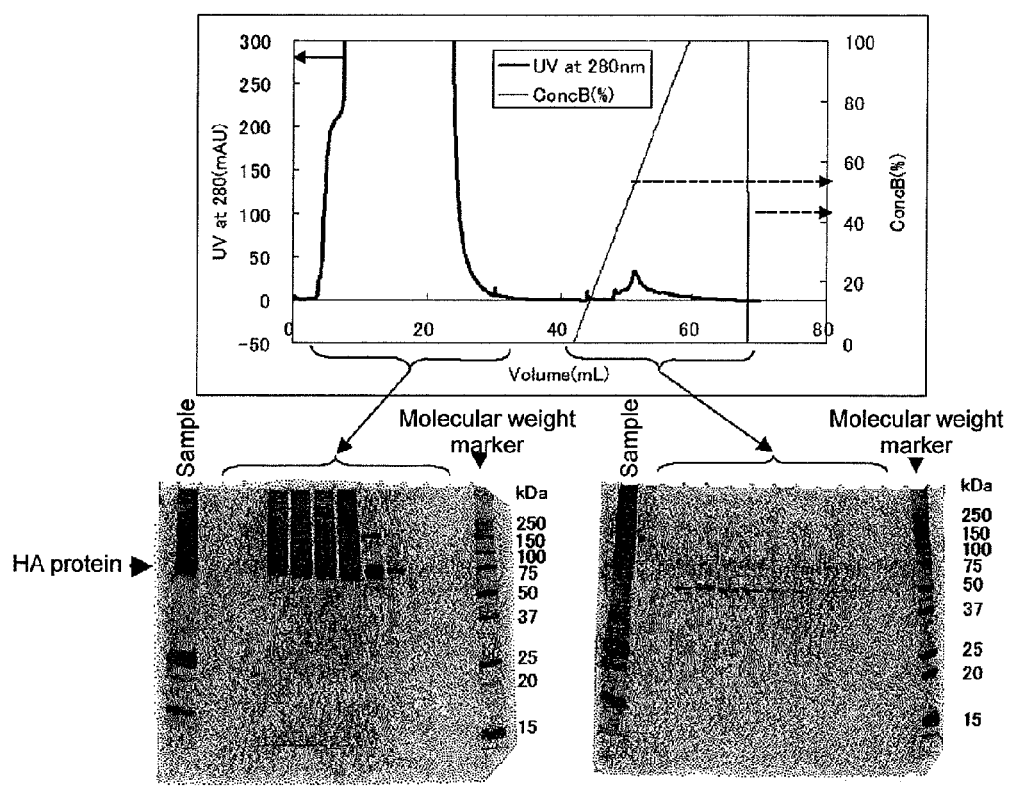
FIG. 1 is a diagram showing the result of hydroxyapatite column chromatography and the result of SDS-PAGE (non-reducing, silver staining) of each of the fractions in Example 1.

The influenza virus antigen may be a part or an equivalent of an influenza virus. Examples of the influenza virus antigen which may be used include proteins existing on the surface of the virus such as HA protein, NA protein and M2 protein; and proteins existing inside the virus such as M1 protein and NP protein; among which HA protein is preferably used. The raw material for the production of HA protein may be culture liquid of an influenza virus or culture liquid of recombinant cells to which an HA protein synthetic gene was incorporated.

The method of the present invention for producing a purified influenza virus antigen comprises the step of treating a sample containing an influenza virus antigen with a surfactant, the step of bringing the sample after the treatment into contact with hydroxyapatite in the presence of the surfactant, and the step of recovering the hydroxyapatite-non-adsorbed fraction. In the method of the present invention, hydroxyapatite is used to make impurities in the sample adsorb thereto to remove the impurities, and the influenza virus antigen is obtained in the non-adsorbed fraction.

Examples of the influenza virus antigen-containing sample to be provided for the method of the present invention include culture liquid prepared by growing an influenza virus by the animal cell culture system using animal cells as the host or the chicken egg culture system using chicken eggs as the host, and culture liquid from a culture system of recombinant cells to which a gene that produces an influenza virus antigen such as the HA protein synthetic gene was incorporated.

In the culture liquid wherein an influenza virus was grown by the chicken egg culture system or the animal cell culture system, a large amount of impurities such as proteins derived from the host are contained. By the method of the present invention, such impurities can be efficiently removed by a simple operation to obtain an influenza virus antigen at high purity.

The animal cell culture system and the chicken egg culture system are known in the art, and any of such known culture systems may be used. In the animal cell culture system, tissues and cultured cells isolated from mammals such as cow, horse, pig, sheep, dog and monkey; birds such as chicken, goose and duck; mouse; and the like may be used, and CHO cells, Vero cells, MDCK cells, Per.C6 cells, EB66 cells and the like are preferably used.

The influenza virus grown in culture liquid is usually separated from the culture liquid by a commonly-used purification step such as ultrafiltration or density gradient centrifugation, to prepare crudely purified influenza virus liquid. In the method of the present invention, such a crudely purified influenza virus liquid may be suitably used as the sample containing an influenza virus antigen.

The sample containing an influenza virus antigen to be provided for the method of the present invention is not limited to an influenza virus culture liquid. An influenza virus antigen produced by introducing a gene that produces an influenza virus antigen to insect cells or animal cells by gene recombination may also be purified by the method of the present invention.

The animal cells and insect cells to which the HA protein gene is to be introduced are not restricted, and examples of the insect cells include cells of *Mamestra* and silkworm, and examples of the animal cells include cells of mammals such as dog, cat, monkey, pig, cow and mouse, and cells of birds such as chicken, goose and duck. The host cells are preferably insect cells, with which high growth efficiency can be attained, and mammal cells, which contain less sources of allergy. Preferred examples of the animal cells include CHO cells, COS cells, HEK293 cells, Vero cells and MDCK cells, and preferred examples of the insect cells include SF-9 cells and SF-21 cells. Further, the base sequences of influenza virus antigens are well known, and examples thereof include the one described in GenBank Accession No. EU103824. Based on this base sequence, an influenza virus antigen can be prepared by gene recombination (see, for example, Non-patent Document 1). Further, influenza virus antigens prepared by gene recombination are commercially available, and such commercially available products may also be applied to the method of the present invention.

As the surfactant to be used for the treatment of an influenza virus antigen-containing sample, one or more selected from nonionic surfactants, amphoteric surfactants and anionic surfactants may be used.

Examples of the nonionic surfactants include polyoxyethylene alkyl ethers (e.g., Emulgen 220, Emulgen 104P, Emulgen 108 and Emulgen 408 (trade names) manufactured by KAO CORPORATION), polyoxyethylene alkyl phenyl ethers (e.g., Emulgen 903, Emulgen 909 and Emulgen 913 (trade names) manufactured by KAO CORPORATION), polyoxyethylene-polyoxypropylene condensates (e.g., Pluronic F88 (trade name) manufactured by ADEKA CORPORATION (Asahi Denka)), acyl polyoxyethylene sorbitan esters (e.g. Tween 21, Tween 81, Tween 20, Tween 40, Tween 60, Tween 80, Tween 85 and Emasol 4130 (trade names)), alkyl polyoxyethylene ethers (e.g., Atlas G2127, Brij 36T and Brij 56 (trade names)), n-dodecyl-β-D-maltoside, sucrose monolaurate, polyoxyethylene lauryl ether (e.g., Emulgen 120 (trade name) manufactured by KAO CORPORATION), polyoxyethylene alkylene phenyl ether (e.g., Emulgen A60 (trade name)), polyoxyethylene alkylene tribenzyl phenyl ether (e.g., Emulgen 66 (trade name)), polyoxyethyleneglycol p-t-octylphenyl ether polyoxyethyleneglycol (Triton X-100 (trade name)), polyoxyethylene higher alcohol ethers (e.g., Emulgen 705 and Emulgen 709 manufactured by KAO CORPORATION), polyoxyethylene aliphatic acid esters, polyoxyethylenesorbitan aliphatic acid esters, sorbitan aliphatic acid esters, polyoxyethylene sorbitol fatty acid esters, polyoxyethylene alkylamine, glycerin fatty acid esters, n-octyl-β-D-glucoside, polyoxyethylene glycol monododecyl ethers, n-octyl-β-D-thioglucoside and polyoxyethylene monolaurate. Especially preferred examples of the nonionic surfactants include polyoxyethyleneglycol p-t-octylphenyl ether.

Examples of the amphoteric surfactants include betaine derivatives, alkylbetaine derivatives, imidazoliumbetaine derivatives, sulfobetaine derivatives, aminocarboxylic acid derivatives, imidazoline derivatives, amine oxanoid derivatives and bile acid derivatives, and especially preferred examples thereof include DDA [(2-(N-Dodecyl-N,N-dimethylamino)Acetate], DDSA [Dodecyldimethyl(3-sulfopropyl)ammonium Hydroxide] and CHAPS [3-(3-cholamidepropyl)dimethylammonio-1-propanesulphonate].

Examples of the anionic surfactants include lauryl sulfuric acid, dodecylsulfonic acid, laurosarcosine, dodecylbenzenesulfonic acid, caseinic acid, lauroyl-β-alanine, cholic acid, deoxycholic acid, chenodeoxycholic acid, taurocholic acid, taurodeoxycholic acid and fatty acid salts. The anionic surfactant may also be an alkaline metal salt of these compounds such as the sodium salt, potassium salt or the like thereof. Sodium deoxycholate (DOC) is preferably used.

These surfactants may be used either solely or as a combination of plural surfactants. In cases where a combination of plural surfactants is used, a nonionic surfactant(s) and an amphoteric surfactant(s) may be used in combination; a nonionic surfactant(s) and an anionic surfactant(s) may be used in combination; an amphoteric surfactant(s) and an anionic surfactant(s) may be used in combination; or these three types of surfactants may be used in combination. Further, nonionic surfactants themselves, amphoteric surfactants themselves or anionic surfactants themselves may be used as a combination with each other.

The surfactant treatment can be carried out by, for example, adding the surfactant(s) to an influenza virus antigen-containing sample followed by stirring the resulting mixture at about 0° C. to about room temperature for about 30 minutes to about 2 hours. The concentration of the surfactant(s) during the treatment (the concentration immediately before the contact with hydroxyapatite) is usually preferably 0.05% to 20%, more preferably 0.1% to 20%, still more preferably 0.1% to 5% in terms of the concentration of the effective component (s) of the surfactant(s) with respect to the total influenza virus antigen-containing sample. However, the surfactant concentration suitable for the treatment varies depending on the type(s) of the surfactant(s), and is not necessarily restricted to the above range. For example, in the case of CHAPS, 0.5% to 20% is preferred, and 1% to 15% is more preferred. In the case of polyoxyethyleneglycol p-t-octylphenyl ether, 0.05% to 3% is preferred, and 0.1% to 2% is more preferred. In the case of deoxycholic acid or a deoxycholate, 1% to 20% is preferred, and 1.5% to 15% is more preferred.

As required, insoluble matters in the sample liquid are removed from the sample after the surfactant treatment. Examples of the method for removing the insoluble matters include centrifugation, ultracentrifugation and filter filtration. By this step of removing insoluble matters, most of the impurities can be removed, so that highly efficient purification is possible when this step is combined with the removal of impurities by adsorption to hydroxyapatite.

Subsequently, the sample liquid after the surfactant treatment is brought into contact with hydroxyapatite. In the present invention, it is important to bring hydroxyapatite into contact with the influenza virus antigen in the presence of a surfactant. It was confirmed that, when hydroxyapatite is brought into contact with an influenza virus antigen-containing sample liquid in the absence of a surfactant, the influenza virus antigen adsorbs to hydroxyapatite (see Reference Example below). Since, in the present invention, a surfactant already exists in the surfactant-treated sample liquid, the liquid after the treatment may be brought into contact with hydroxyapatite as it is. Further addition of a surfactant(s) to the liquid after the treatment may also be carried out.

The contact of the surfactant-treated sample liquid with hydroxyapatite is preferably carried out under the condition of preferably pH 6 to 10, more preferably pH 6 to 9, still more preferably pH 6.5 to 9. In cases where pH is lower than this range, it is difficult to obtain an influenza virus antigen in the non-adsorbed fraction, and, in cases where pH is higher than this range, the efficiency of removal of impurities by adsorption decreases (see Examples below).

The type of hydroxyapatite to be used in the present invention is not restricted, and any hydroxyapatite which is commercially available may be used. For example, hydroxyapatite commercially available as a filler for columns may be used. Preferred examples of the hydroxyapatite include ceramic hydroxyapatite having a particle diameter of about 20 to 50 μm and a pore size of about 800 angstroms. Examples of such a commercially available hydroxyapatite include "Ceramic Hydroxyapatite Type I" and "Ceramic Hydroxyapatite Type II" sold by Bio-Rad.

The practical operation of bringing the surfactant-treated sample into contact with hydroxyapatite is not restricted, and may be selected appropriately based on the concentration and the amount of the sample, the form of the hydroxyapatite to be used, and the like. Examples thereof include the batchwise operation wherein hydroxyapatite is fed to the sample, and a method wherein the sample is added to a column filled with hydroxyapatite.

In the batchwise method, for example, insoluble matters are removed from the surfactant-treated sample by filtration, centrifugation and/or the like, followed by feeding hydroxyapatite to the sample. The sample may be preliminarily adjusted to about pH 6 to 10, preferably about pH 6 to 9, more preferably pH 6.5 to 9 with an appropriate buffer or the like. A surfactant may be further added to the sample, but, since a surfactant already exists in the sample after the treatment, the operation can be simply carried out just by adding hydroxyapatite without further addition of the surfactant. After feeding hydroxyapatite to the sample, these are brought into contact with each other at about 0° C. to about room temperature by stirring as appropriate for about 15 minutes to 1 hour, thereby making impurities in the sample adsorb to hydroxyapatite. Since the purified influenza virus antigen can be obtained in the non-adsorbed fraction, the supernatant is recovered by removing hydroxyapatite by filtration or the like.

In the method wherein a column is filled with hydroxyapatite, for example, the column is equilibrated with a buffer such as phosphate buffer, and a surfactant-treated sample is then injected into the column, followed by developing the sample with the buffer used for the equilibration or the like Since the influenza virus antigen passes through the column without adsorbing to hydroxyapatite, a purified influenza virus antigen can be obtained by fractionating the non-adsorbed fraction. The eluted fraction contains mainly HA protein, and the influenza virus antigen is already purified to a considerable degree. However, further purification may be carried out by repeating the same chromatography, and, if necessary, further purification may be carried out by a method such as ultrafiltration, ion-exchange chromatography and/or gel filtration. pH of the buffer is preferably 6 to 10, more preferably 6 to 9, still more preferably 6.5 to 9.

Examples of the buffer which may be used include, in addition to phosphate buffer, MES[2-(N-morpholino)ethanesulfonic acid], BIS-TRIS [bis-(2-hydroxyethyl)-amino]tris-(hydroxymethyl)methane], ADA [N-2-acetamido imino diacetic acid monosodium salt], ACES [N-2-acetamido-2-aminoethanesulfonic acid], PIPES [piperazine-N,N'-bis(2-ethane-sulfonic acid)], MOPSO [(3-N-morpholino)-2-hydroxypropanesulfonic acid], BIS-TRIS PROPANE [1,3-bis [tris(hydroxymethyl)methylamino]propane], BES [N,N-bis-(2-hydroxyethyl)-2-amino-ethanesulfonic acid], TES [N-tris (hydroxymethyl)methyl-2-aminoethane-sulfonic acid and 2-2([2-hydroxy-1,1-bis(hydroxymethyl)ethyl]amino) ethanesulfonic acid], HEPES [N-2-hydroxyethylpiperazine-N'-2-ethane-sulfonic acid], DIPSO [3-(N,N-bis(2-hydroxy-ethyl)amino)-2-hydroxy-propanesulfonic acid], TAPSO [3-N-tris(hydroxymethyl)methylamino]-2-hydroxy-propanesulfonic acid], TRIS [tris-(hydroxymethyl)-aminomethane], HEPPSO [N-(2-hydroxyethyl)-piperazine-N'-[2-hydroxy-propanesulfonic acid], POPSO [(piperazine-N, N'-bis[2-(hydroxypropanesulfonic acid)], EPPS [N-[2-hydroxyethyl]-piperazine-N'-[3-propanesulfonic acid and HEPPS], TEA [triethanolamine], TRICINE [N[tris-(hydroxymethyl)methyl]glycine], BICINE [N,N-bis-(2-hydroxyethyl)]-glycine), TAPS [3-{[tris-(hydroxymethyl)methyl]amino}-propanesulfonic acid], imidazole, HEPPS [N-2-hydroxyethylpiperazine-N'-3-propane-sulfonic acid], glycine amide hydrochloride, glycylglycine, citrate, acetate, borate and succinate buffer.

Further, these buffers may contain salts and/or surfactants. Examples of the salts which may be used include sodium salts, potassium salts, ammonium salts, magnesium salts, calcium salts, chlorides, bromides, acetates, citrates and phosphates. More particular examples thereof include sodium chloride, potassium chloride, ammonium chloride, magnesium chloride, calcium chloride, sodium bromide, potassium bromide, ammonium bromide, sodium citrate, potassium citrate, ammonium citrate, sodium acetate, potassium acetate, calcium acetate, magnesium acetate, sodium phosphate, potassium phosphate and ammonium phosphate. Examples of the surfactants which may be used include those described above, but the surfactants are not restricted thereto.

Those skilled in the art can appropriately select a suitable composition of the buffer according to the knowledge known in the art.

The surfactant contained in the non-adsorbed fraction after the contact with hydroxyapatite can be removed as appropriate by ultrafiltration and/or the like.

The thus purified influenza virus antigen is highly pure, and hardly contains impurities such as a surfactant and DNAs derived from the chicken egg, animal cells or recombinant cells. The influenza virus antigen may be used as an influenza vaccine after addition of an adjuvant, antiseptic and/or the like thereto. The influenza vaccine may be filled into a syringe, cartridge which may be used for an inoculation operation, or the like, to prepare a prefilled kit with which inoculation is possible, such as a prefilled syringe.

The purified influenza virus antigen liquid obtained as the non-adsorbed fraction may be used as it is, as a composition for diagnosis, or the like, to provide a part of a diagnostic kit for influenza. Further, it is also possible to prepare an anti-influenza antibody using the purified influenza virus antigen as an immunogen by a well-known method, and then to use a reagent containing this antibody as a part of a diagnostic reagent for influenza or a part of a diagnostic kit for influenza.

EXAMPLES

The present invention is described more concretely based on the Examples below. It should be noted, however, that the present invention is not restricted to the Examples below.

Example 1

To cultured Madin Darby canine kidney (MDCK) cells, influenza virus (the H1N1 strain) was inoculated, and the virus was grown. The obtained culture supernatant was crudely purified by filtration, ultrafiltration and sucrose density gradient centrifugation, followed by inactivation of the influenza virus with β-propiolactone. The inactivated influenza virus liquid was subjected to ultrafiltration to replace the solvent with 6.7 mM phosphate buffered saline, to obtain a crudely purified influenza virus liquid.

To 10 mL of the crudely purified influenza virus liquid, 10 mL of 6.7 mM phosphate buffered saline containing 10% CHAPS was added, and the resulting mixture was stirred at room temperature for 1 hour, followed by ultracentrifugation at 200,000×g for 30 minutes at 15° C. Thereafter, the supernatant was collected to provide a sample for column chromatography.

In a column having an inner diameter of 0.5 cm and a height of 16 cm, 1.8 mL of a hydroxyapatite resin (Macro-Prep Ceramic Hydroxyapatite Type I 40 µm, manufactured by Bio-Rad) was filled, and the column was then equilibrated with 5 mM phosphate buffer (pH 7.0) at a flow rate of 0.5 mL/min., followed by adding 20 mL of the sample to the column and developing the sample with 5 mM phosphate buffer (pH 7.0). The pass-through fraction (non-adsorbed fraction) was collected to provide a purified influenza virus antigen liquid. The adsorbed fraction was eluted with a linear gradient of 5 mM to 400 mM phosphate buffer. The purified influenza virus antigen liquid was further subjected to ultrafiltration using VIVAFLOW 50 (manufactured by Sartorius) to remove CHAPS and replace the solvent with 6.7 mM phosphate buffered saline, followed by filter filtration using a 0.22 µm filter (manufactured by Millipore, SLLG025SS), to obtain 15 mL of a purified influenza virus antigen liquid.

Figure 2:
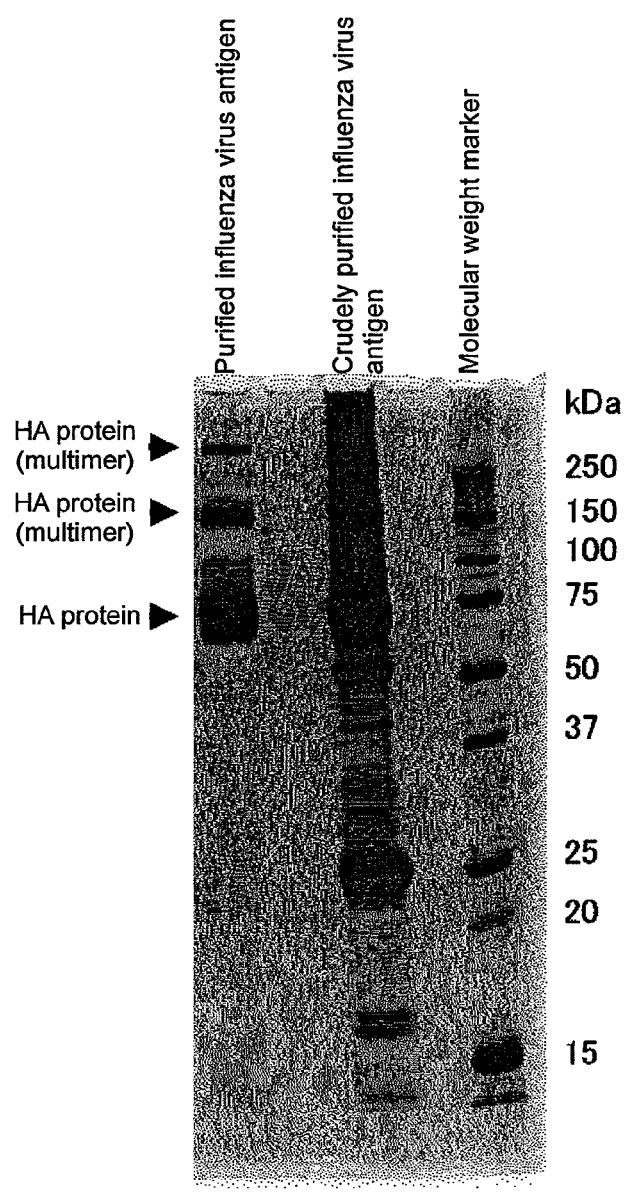
FIG. 2 is a diagram showing the result of SDS-PAGE (non-reducing, silver staining) of the sample before and after the purification with hydroxyapatite in Example 1.
Figure 3:
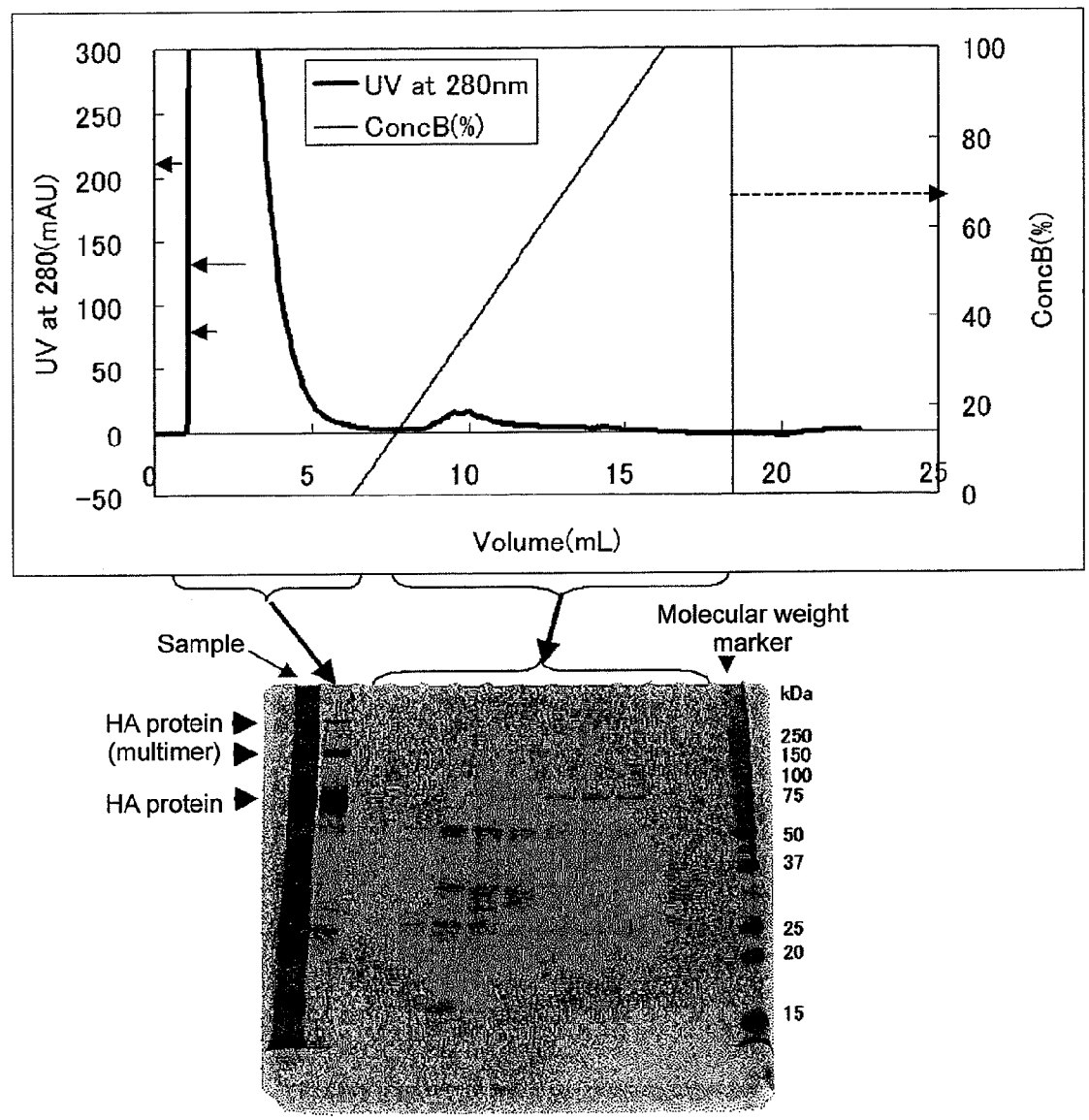
FIG. 3 is a diagram showing the result of hydroxyapatite column chromatography and the result of SDS-PAGE (non-reducing, silver staining) of each of the fractions in Example 2.
Figure 4:
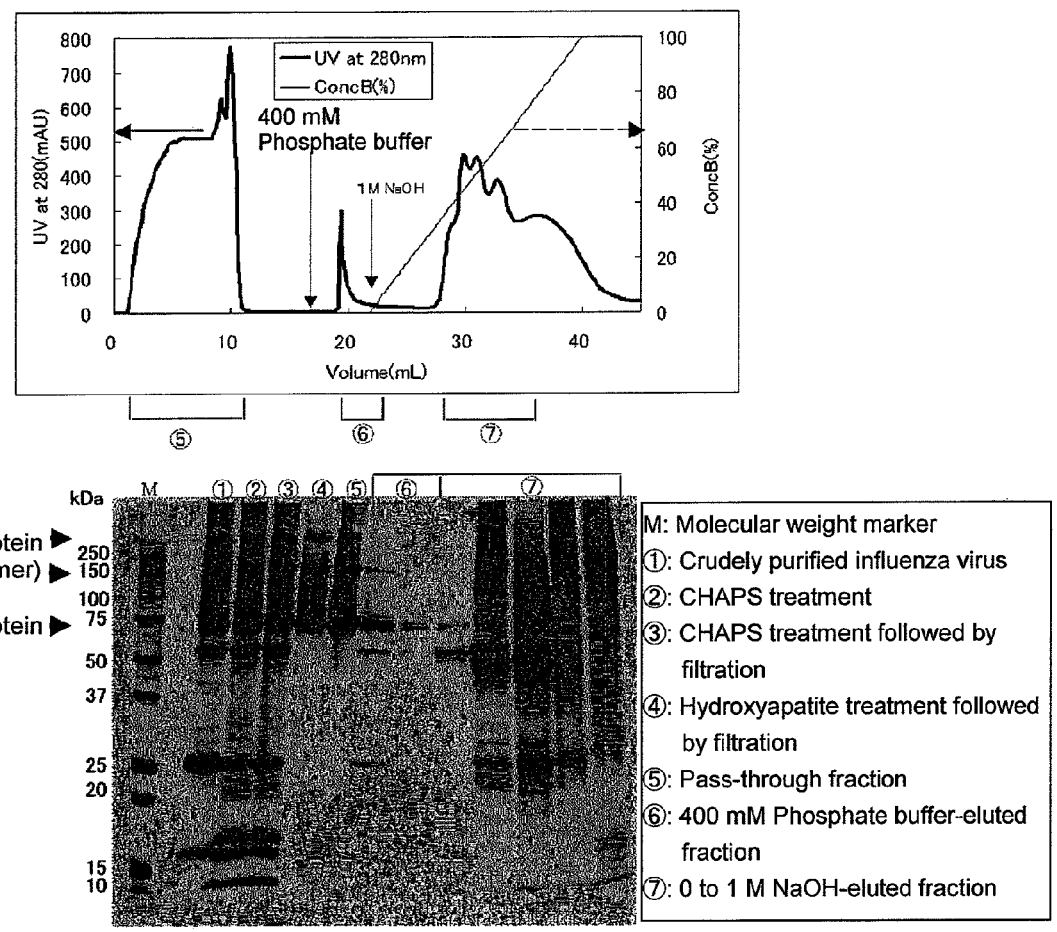
FIG. 4 is a diagram showing the result of hydroxyapatite column chromatography and the result of SDS-PAGE (non-reducing, silver staining) of each of the fractions in Example 3.
Figure 5:
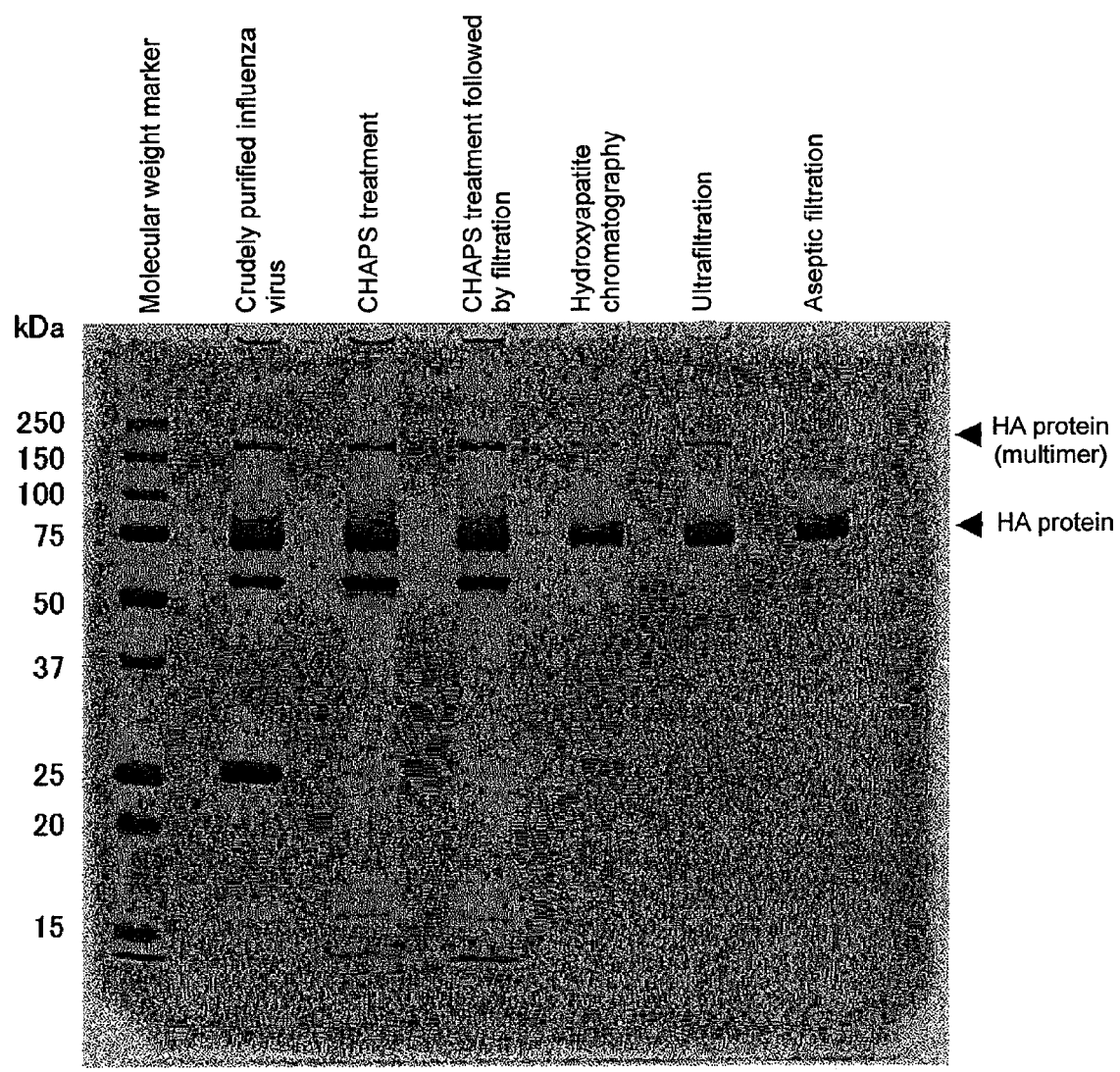
FIG. 5 is a diagram showing the result of SDS-PAGE (non-reducing, CBB staining) of the sample in each purification step in Example 3.

The results of hydroxyapatite column chromatography and SDS-PAGE (non-reducing, silver staining) of each fraction are shown in FIG. 1. The gradient was prepared by mixing A solution (5 mM phosphate buffer) with B solution (400 mM phosphate buffer), and ConcB (%) in the figure indicates the mixing ratio of B solution (e.g., ConcB 0% solution means 100% A solution+0% B solution; ConcB 50% solution means 50% A solution+50% B solution; and ConcB 100% solution means 0% A solution+100% B solution). Further, the results of SDS-PAGE (non-reducing, silver staining) before and after the purification are shown in FIG. 2, and the results of DNA analysis, CHAPS analysis and total protein mass analysis of the purified influenza antigen are shown in Table 1. The HA protein content in Table 1 is a value obtained by carrying out CBB staining after the SDS-PAGE and calculating the HA protein content by image analysis, followed by multiplying the resulting value by the total protein amount.

The recovery of HA protein calculated from the HA content was 72%. Further, impurities such as the DNAs derived from the host and CHAPS added during the purification steps had been removed during a series of purification steps to very low levels.

TABLE 1

| Sample | DNA content (ng/mL) | CHAPS (μg/mL) | Total protein amount (mg) | HA content* (mg) |
|---|---|---|---|---|
| Crudely purified influenza virus | 70 | — | 15.5 | 5.4 |
| Purified influenza virus antigen | 1.62 | 10 | 4.0 | 3.9 |

Example 2

In the same manner as in Example 1, a crudely purified influenza virus liquid was prepared from culture liquid of an influenza virus (the H1N1 strain) prepared by growing the virus with MDCK cells. To 1 mL of the crudely purified liquid, 1 mL of 6.7 mM phosphate buffered saline containing 1% Triton X-100 was added, and the resulting mixture was stirred at room temperature for 1 hour, followed by ultracentrifugation at 200,000×g for 30 minutes at 15° C. Thereafter, the supernatant was recovered to provide a sample for column chromatography.

In a column having an inner diameter of 0.5 cm and a height of 9 cm, 1 mL of a hydroxyapatite resin (Macro-Prep Ceramic Hydroxyapatite Type I 40 μm, manufactured by Bio-Rad) was filled, and the column was then equilibrated with 5 mM phosphate buffer (pH 7.0) at a flow rate of 0.5 mL/min., followed by adding 2 mL of the sample to the column and developing the sample with 400 mM phosphate buffer (pH 7.0). The pass-through fraction (non-adsorbed fraction) was fractionated to provide a purified influenza virus antigen liquid. The adsorbed fraction was eluted with a linear gradient of 5 mM to 400 mM phosphate buffer.

The results of hydroxyapatite column chromatography and SDS-PAGE (non-reducing, silver staining) of each fraction are shown in FIG. 3. ConcB (%) in the figure has the same meaning as in Example 1.

It was shown that, also in cases where Triton X-100 is used as the surfactant, a purified influenza virus antigen can be efficiently produced by using hydroxyapatite.

Example 3

An influenza virus (the H1N1 strain) was inoculated to an embryonated chicken egg, and the virus was grown. The culture liquid of influenza virus released into the allantoic fluid was crudely purified by ultrafiltration, barium treatment and sucrose density gradient centrifugation, and the influenza virus was inactivated with β-propiolactone. The inactivated influenza virus liquid was subjected to ultrafiltration to replace the solvent with 6.7 mM phosphate buffered saline, to obtain a crudely purified influenza virus liquid.

To 5 mL of the crudely purified influenza virus liquid, 5 mL of 6.7 mM phosphate buffered saline containing 10% CHAPS was added, and the resulting mixture was stirred at room temperature for 1 hour, followed by filtration of the mixture with a membrane filter having a pore diameter of 0.22 μm. The obtained filtrate was used as the sample for column chromatography.

In a column having an inner diameter of 0.5 cm and a height of 16 cm, 1.8 mL of a hydroxyapatite resin (Macro-Prep Ceramic Hydroxyapatite Type I 40 μm, manufactured by Bio-Rad) was filled, and the column was then equilibrated with 5 mM phosphate buffer (pH 7.0) at a flow rate of 0.5 mL/min., followed by adding 6 mL of the sample to the column and developing the sample with 5 mM phosphate buffer (pH 7.0). The pass-through fraction (non-adsorbed fraction) was fractionated to provide a purified influenza virus antigen liquid. The purified influenza virus antigen liquid was further subjected to ultrafiltration using VIVAFLOW 50 (manufactured by Sartorius) to remove CHAPS and replace the solvent with 6.7 mM phosphate buffered saline, followed by filtration using a 0.22 μm filter (manufactured by Millipore, SLLG025SS) (aseptically), to obtain 15 mL of a purified influenza virus antigen liquid. The adsorbed fraction was eluted with 400 mM phosphate buffer (pH 7.0) and then with a linear gradient of 0 M to 1 M NaOH, to obtain an eluted fraction.

The results of hydroxyapatite column chromatography and SDS-PAGE (non-reducing, silver staining) of each fraction are shown in FIG. 4. The gradient was prepared by mixing A solution (400 mM phosphate buffer) with B solution (1M NaOH), and ConcB (%) in the figure indicates the mixing ratio of B solution. The result of SDS-PAGE (non-reducing, CBB staining) of the sample from each purification step is shown in FIG. 5. Further, the results of analyses of the total protein mass and CHAPS in the purified influenza virus antigen are shown in Table 2. The HA protein content in the table is a value obtained by carrying out CBB staining after the SDS-PAGE and calculating the HA protein content by image analysis, followed by multiplying the resulting value by the total protein amount.

The recovery of HA protein calculated from the HA protein content was 42%. Further, CHAPS added during the purification steps had been removed during a series of purification steps to a very low level.

TABLE 2

| Sample | CHAPS (μg/mL) | Total protein amount (mg) | HA content* (mg) |
|---|---|---|---|
| Crudely purified influenza virus | — | 6.0 | 3.1 |
| Purified influenza virus antigen | 0.44 | 1.3 | 1.3 |

Example 4

In the same manner as in Example 1, a crudely purified influenza virus liquid was prepared from an influenza virus (the H1N1 strain) prepared by growing the virus with MDCK cells. To 1 mL of the crudely purified liquid, 1 mL of 6.7 mM phosphate buffered saline containing 1% Triton X-100 was added, and the resulting mixture was stirred at room temperature for 1 hour, followed by carrying out ultracentrifugation at 200,000×g for 30 minutes at 15° C. and recovering the supernatant. To 0.2 mL of the supernatant, 0.2 mL of a hydroxyapatite resin (Macro-Prep Ceramic Hydroxyapatite Type I 40 μm, manufactured by Bio-Rad) was added, and the resulting mixture was stirred for 30 minutes, followed by transferring the mixture to a centrifugal filtration filter (Ultrafree-MC, manufactured by Millipore), carrying out centrifugation at 15,000×g for 30 seconds and collecting the permeate as the non-adsorbed fraction. To the hydroxyapatite resin remained on the upper side, 0.25 mL of 6.7 mM phosphate buffered saline was added, and the resulting mixture was stirred, followed by 3 times of the operation of centrifuging and washing in the same manner, after which the permeate was collected as the wash fraction. Subsequently, 250 mM phosphate buffer was added to the resin and the resulting mixture was stirred, followed by centrifuging the mixture in the same manner to carry out elution, after which the permeate was collected as the eluted fraction (phosphate). Further, 0.25 mL of 0.1 M NaOH solution was added to the resin and centrifugation was carried out in the same manner to carry out elution, after which the permeate was collected as the eluted fraction (NaOH). The obtained permeate was subjected to SDS-PAGE (non-reducing, CBB staining). The results are shown in FIG. 6.

Example 5

In the same manner as in Example 1, a crudely purified influenza virus liquid was prepared from influenza virus (the H1N1 strain) grown with MDCK cells. To 0.15 mL of the crudely purified liquid, 0.15 mL of 6.7 mM phosphate buffered saline supplemented with various surfactants at the concentrations shown in Table 3 was added. That is, the surfactant concentration in the surfactant treatment system was a half of the concentration described in Table 3. After stirring the mixture at room temperature for 1 hour, the mixture was subjected to ultracentrifugation at 550,000×g at 15° C. for 30 minutes. Thereafter, the supernatant and precipitate fractions were collected respectively, and subjected to SDS-PAGE (non-reducing, CBB staining). The results are shown in FIG. 7. As is evident from FIG. 7, the supernatant prepared by adding CHAPS and carrying out ultracentrifugation contained the smallest amount of proteins other than HA protein, which are impurities. It was shown that, in cases where CHAPS is used, an influenza virus antigen can be highly purified even at the stage of surfactant treatment. In the table, "DOC" means sodium deoxycholate.

TABLE 3

| Surfactant | Concentration (%) |
|---|---|
| TritonX-100 | 1 |
| Tween80/CTAB | 0.06/0.15 |
| CHAPS | 10 |
| DOC | 10 |

Example 6

In the same manner as in Example 1, a crudely purified influenza virus liquid was prepared from an influenza virus (the H1N1 strain) prepared by growing the virus with MDCK cells. To 1 mL of the crudely purified liquid, 10 mL of 6.7 mM phosphate buffer containing 1% Triton X-100 was added, and the resulting mixture was stirred at room temperature for 1 hour, followed by ultracentrifugation at 200,000×g for 30 minutes at 15° C. Thereafter, the supernatant was recovered to provide a sample for column chromatography.

Figure 8:
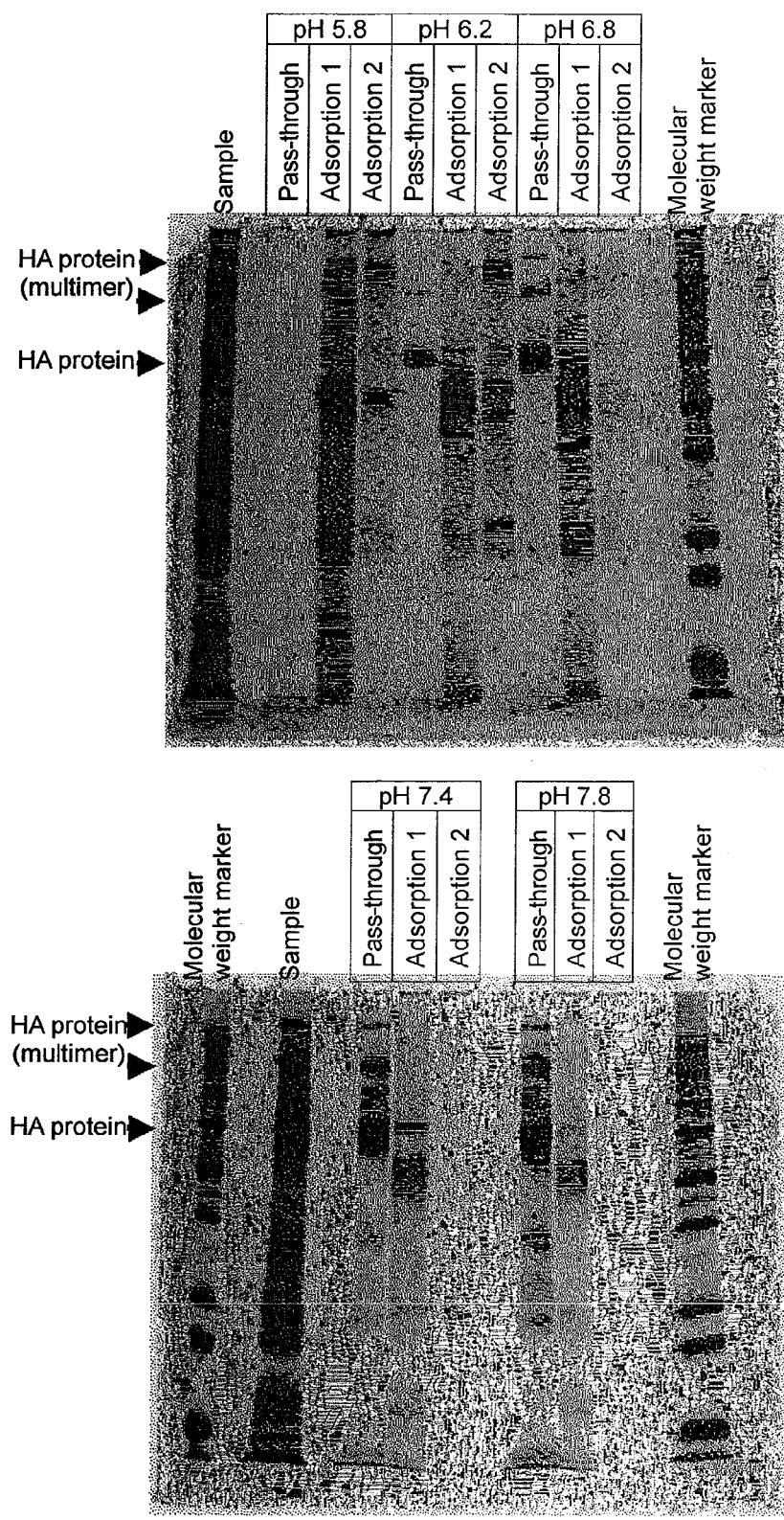
FIG. 8 is a diagram showing the result of SDS-PAGE (non-reducing, silver staining) of each of the fractions obtained in Example 6.

In a column having an inner diameter of 0.5 cm and a height of 9 cm, 1 mL of a hydroxyapatite resin (Macro-Prep Ceramic Hydroxyapatite Type I 40 μm, manufactured by Bio-Rad) was filled, and the column was then equilibrated with 5 mM phosphate buffer at various pH at a flow rate of 0.5 mL/min, followed by adding 1 mL of the sample to the column. The sample was developed with 5 mM phosphate buffer at various pH, and the pass-through fraction (non-adsorbed fraction) was fractionated. The adsorbed fraction was eluted with a stepwise gradient of 0 M to 0.1 M NaOH (A solution: 5 mM phosphate buffer, B solution: 0.1 M NaOH solution), thereby obtaining adsorption fractions 1 and 2. These fractions were subjected to SDS-PAGE (non-reducing, silver staining), and the results are shown in FIG. 8. At pH 5.8, protein could be hardly observed in the pass-through fraction, and most of the proteins including the influenza virus antigen adsorbed to the hydroxyapatite resin. At pH 6.2 or higher, existence of proteins including mainly HA protein was confirmed in the pass-through fraction.

Example 7

In the same manner as in Example 3, a crudely purified influenza virus liquid was prepared from an influenza virus (the H1N1 strain) grown by inoculation to an embryonated chicken egg. To 1 mL of the crudely purified liquid, 1 mL of 6.7 mM phosphate buffer containing 5% sodium deoxycholate (DOC) was added, and the resulting mixture was stirred at room temperature for 1 hour, followed by filtration of the mixture through a membrane filter having a pore diameter of 0.22 μm, to provide the filtrate as the sample for column chromatography.

In a column having an inner diameter of 0.5 cm and a height of 9 cm, 0.9 mL of a hydroxyapatite resin (Macro-Prep Ceramic Hydroxyapatite Type II 40 μm, manufactured by Bio-Rad) was filled, and the column was then equilibrated with 5 mM phosphate buffer (pH 7.0) containing 60 mM NaCl at a flow rate of 0.5 mL/min, followed by adding 1 mL of the sample to the column and developing the sample with 5 mM phosphate buffer (pH 7.0) containing 60 mM NaCl. The pass-through fraction was fractionated to obtain a purified influenza virus antigen liquid. The adsorbed fraction was eluted with 400 mM phosphate buffer and then with a linear gradient of 0 M to 1 M NaOH in the same manner as in Example 3.

Figure 9:
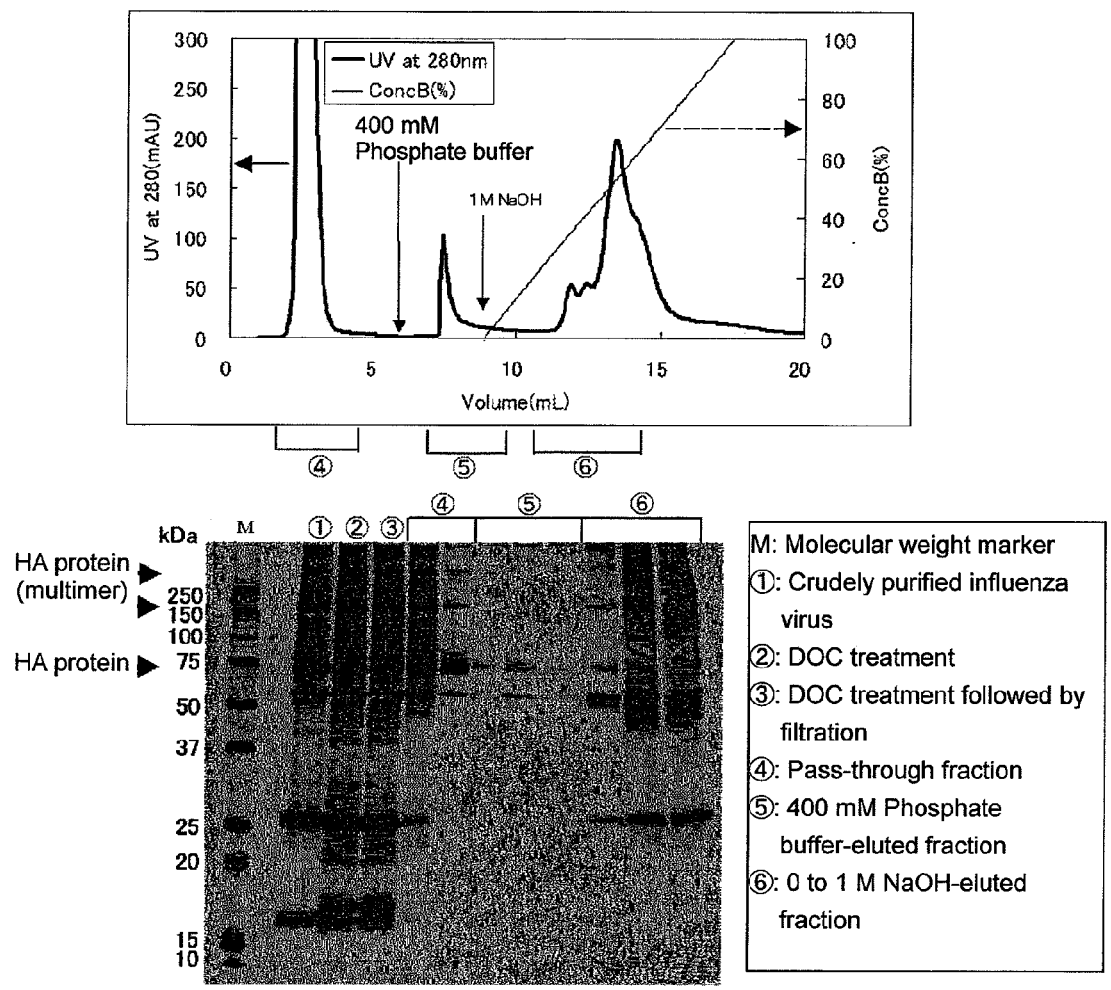
FIG. 9 is a diagram showing the result of hydroxyapatite column chromatography and the result of SDS-PAGE (non-reducing, silver staining) of each of the fractions in Example 7.

The results of hydroxyapatite column chromatography and SDS-PAGE (non-reducing, silver staining) of each fraction are shown in FIG. 9. ConcB (%) in the figure has the same meaning as in Example 3.

It was shown that, also in cases where DOC is used as the surfactant, an influenza virus antigen can be efficiently purified by using hydroxyapatite.

Reference Example

In the same manner as in Example 1, a purified influenza virus antigen was prepared by purification using a hydroxyapatite resin and removal of CHAPS. To 0.5 mL of the purified influenza virus antigen, 0.5 mL of 6.7 mM phosphate buffer, or 0.5 mL of 6.7 mM phosphate buffer containing 10% CHAPS, was added to provide a sample to which CHAPS was not added or a sample to which CHAPS was added, respectively.

In a column having an inner diameter of 0.5 cm and a height of 9 cm, 0.9 mL of a hydroxyapatite resin (Macro-Prep Ceramic Hydroxyapatite Type I 40 μm, manufactured by Bio-Rad) was filled, and the column was then equilibrated with 5 mM phosphate buffer (pH 7.0) at a flow rate of 0.5 mL/min., followed by adding 0.5 mL of the sample, which was then developed with 5 mM phosphate buffer (pH 7.0). The pass-through fraction (non-adsorbed fraction) was fractionated in an amount of 1 mL each. The adsorbed fraction was eluted in the same manner as in Example 1 with a linear gradient of 5 mM to 400 mM phosphate buffer (pH 7.0), while collecting aliquots of 1 mL.

Figure 10:
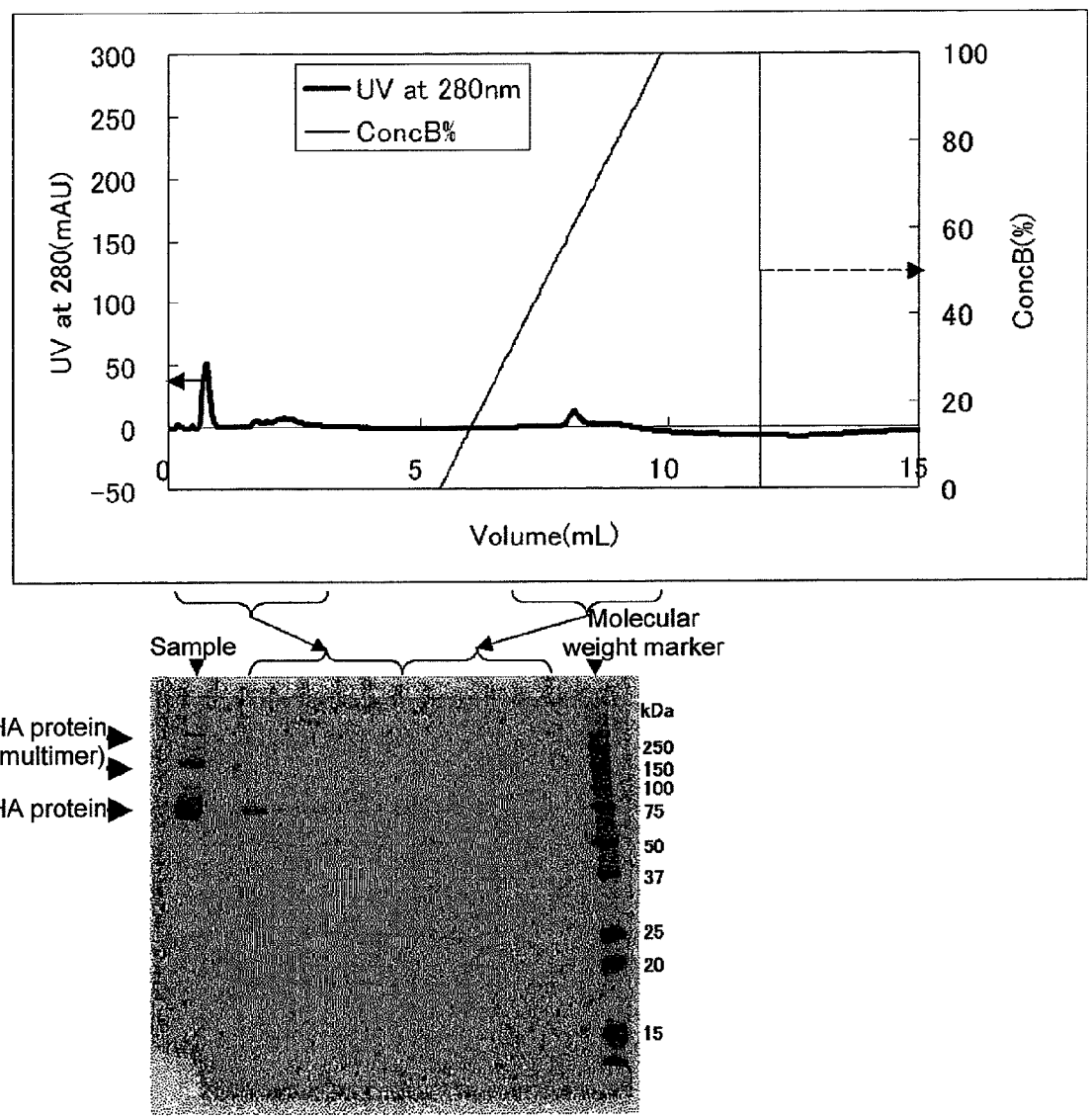
FIG. 10 is a diagram showing the result of hydroxyapatite column chromatography of the sample to which CHAPS was not added and the result of SDS-PAGE (non-reducing, CBB staining) of each of the fractions in Reference Example.
Figure 11:
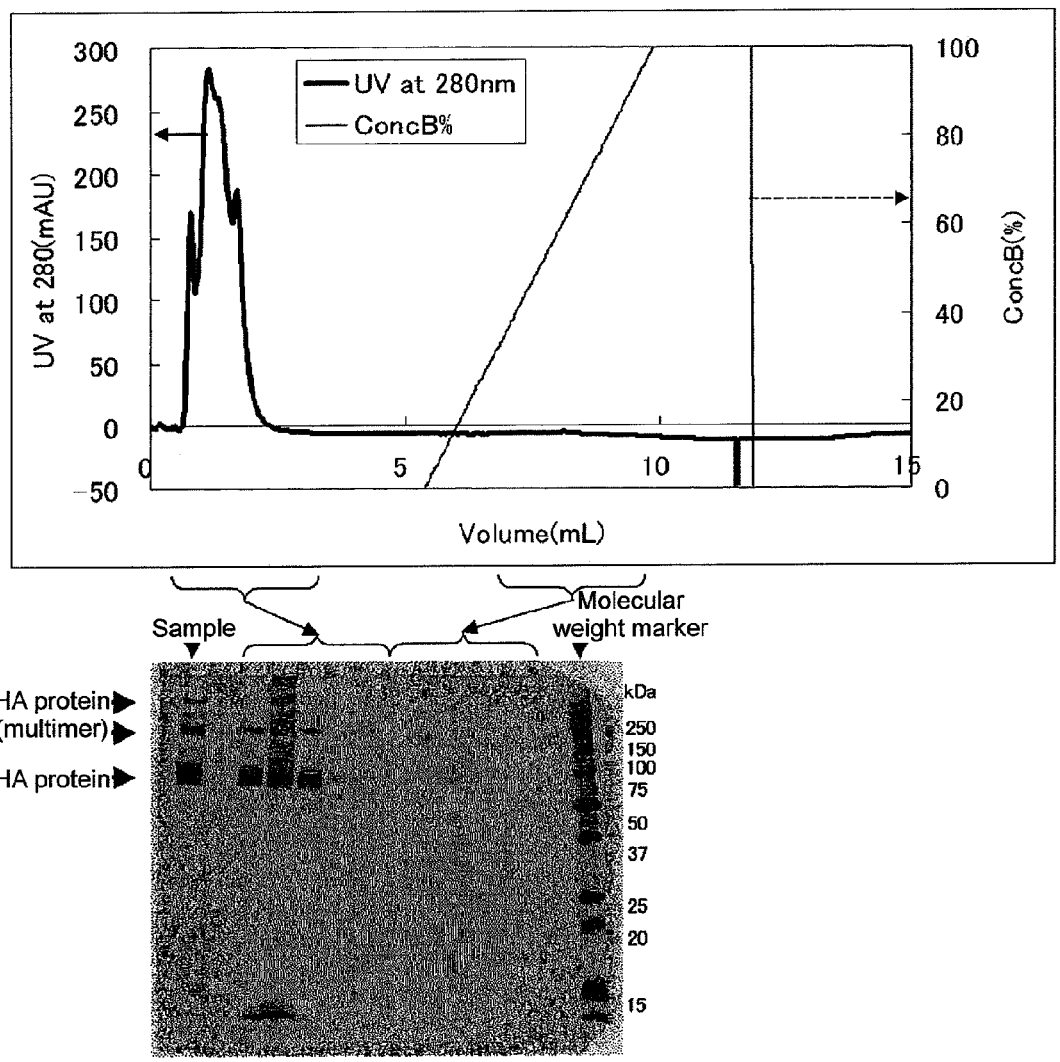
FIG. 11 is a diagram showing the result of hydroxyapatite column chromatography of the sample to which CHAPS was added and the result of SDS-PAGE (non-reducing, CBB staining) of each of the fractions in Reference Example.

The results of hydroxyapatite column chromatography and SDS-PAGE (non-reducing, CBB staining) of each fraction of the sample to which CHAPS was not added are shown in FIG. 10, and the results for the sample to which CHAPS was added are shown in FIG. 11. ConcB (%) in the figures has the same meaning as in Example 1.

In terms of the sample to which CHAPS was not added, most of HA protein adsorbed, and even the elution with 400 mM phosphate buffer allowed only a small amount of elution. On the other hand, in terms of the sample to which CHAPS was added, HA protein was eluted into the pass-through fraction.

Example 8

To cultured Madin Darby canine kidney (MDCK) cells, influenza virus (the H5N1 strain) was inoculated, and the virus was grown. The obtained culture supernatant was crudely purified by filtration, ultrafiltration and sucrose density gradient centrifugation, followed by inactivation of the influenza virus with β-propiolactone. The inactivated influenza virus liquid was subjected to ultrafiltration to replace the solvent with 6.7 mM phosphate buffered saline, to obtain a crudely purified influenza virus liquid.

To 75 mL of the crudely purified influenza virus liquid, 75 mL of 6.7 mM phosphate buffer containing 1% Triton X-100 was added, and the resulting mixture was stirred at room temperature for 90 minutes, followed by filter filtration using a 0.22 μm filter (manufactured by Millipore, Stericup-GV), to provide a sample for column chromatography.

In a column having an inner diameter of 2.6 cm and a height of 20 cm, 56 mL of a hydroxyapatite resin (Macro-Prep Ceramic Hydroxyapatite Type I 40 μm, manufactured by Bio-Rad) was filled, and the column was then equilibrated with 5 mM phosphate buffer (pH 7.0) containing 60 mM NaCl and 0.5% Triton X-100 at a flow rate of 0.5 mL/min., followed by adding 150 mL of the sample to the column and developing the sample with the buffer used for the equilibration. The pass-through fraction (non-adsorbed fraction) was fractionated to provide a purified influenza virus antigen liquid. The adsorbed fraction was eluted with 400 mM phosphate buffer (pH 7.0) and then with a linear gradient of 0 M to 1 M NaOH, to obtain an eluted fraction. From the purified influenza virus antigen liquid, Triton X-100 was removed by ion-exchange chromatography, and the solvent was replaced with 6.7 mM phosphate buffered saline by ultrafiltration using VIVAFLOW 50 (manufactured by Sartorius), followed by filter filtration using a 0.22 μm filter (manufactured by Millipore, MILLEX-GV), thereby obtaining 20 mL of a purified influenza virus antigen liquid.

Figure 12:
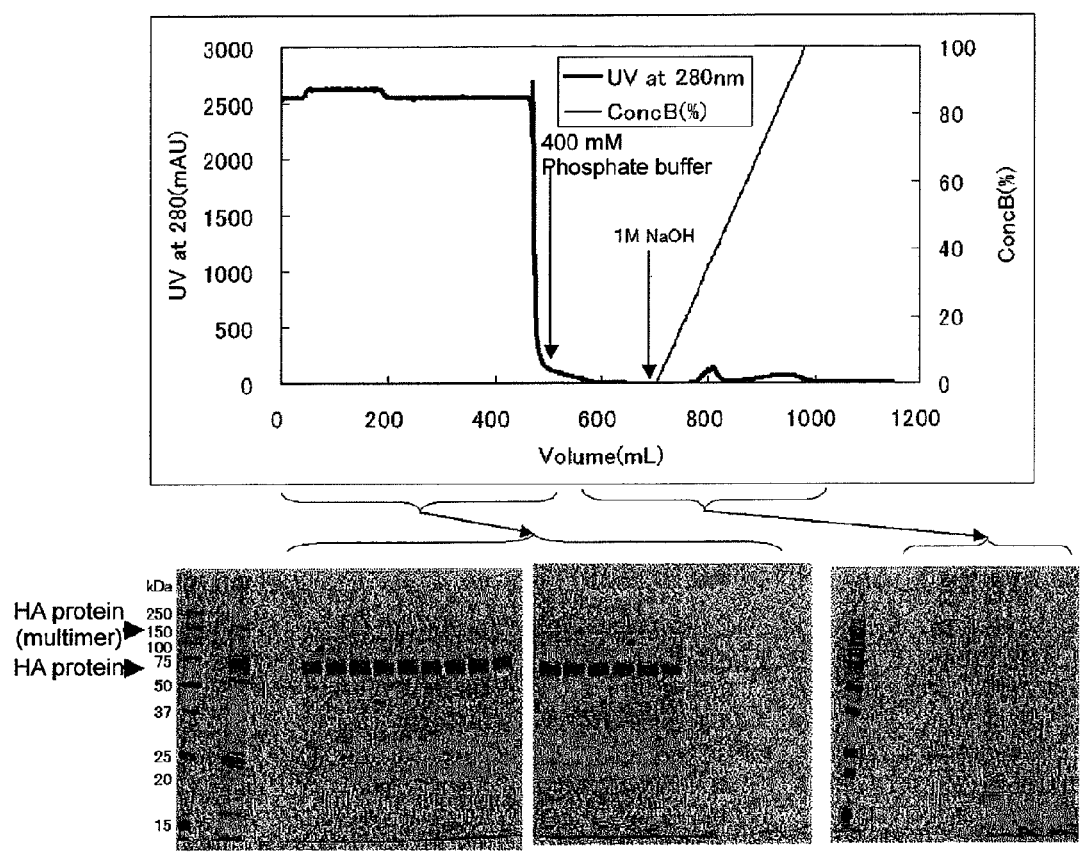
FIG. 12 is a diagram showing the result of hydroxyapatite column chromatography and the result of SDS-PAGE (non-reducing, silver staining) of each of the fractions in Example 8.
Figure 13:
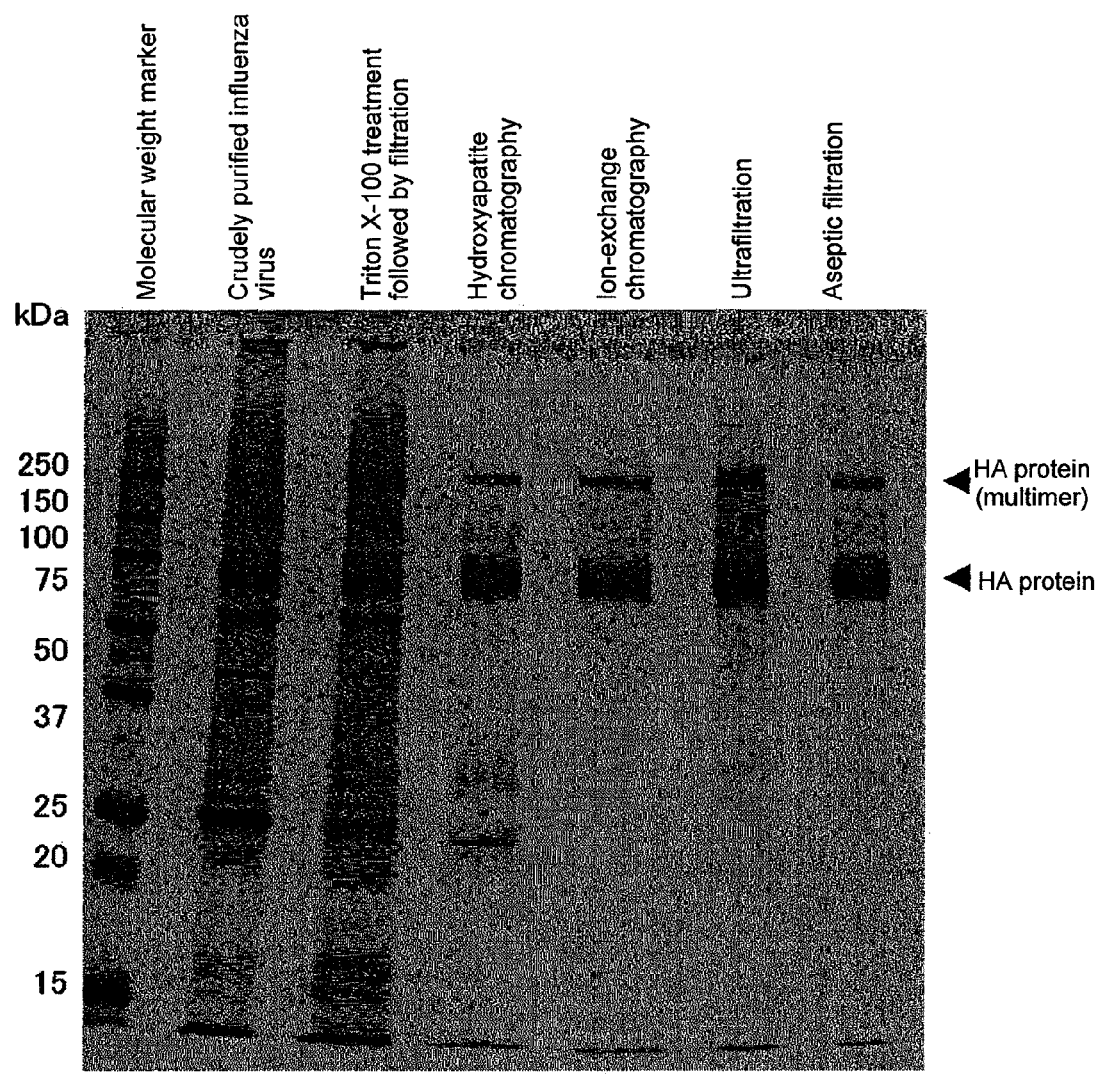
FIG. 13 is a diagram showing the result of SDS-PAGE (non-reducing, silver staining) of the sample before and after the purification with hydroxyapatite in Example 8.
Figure 14:
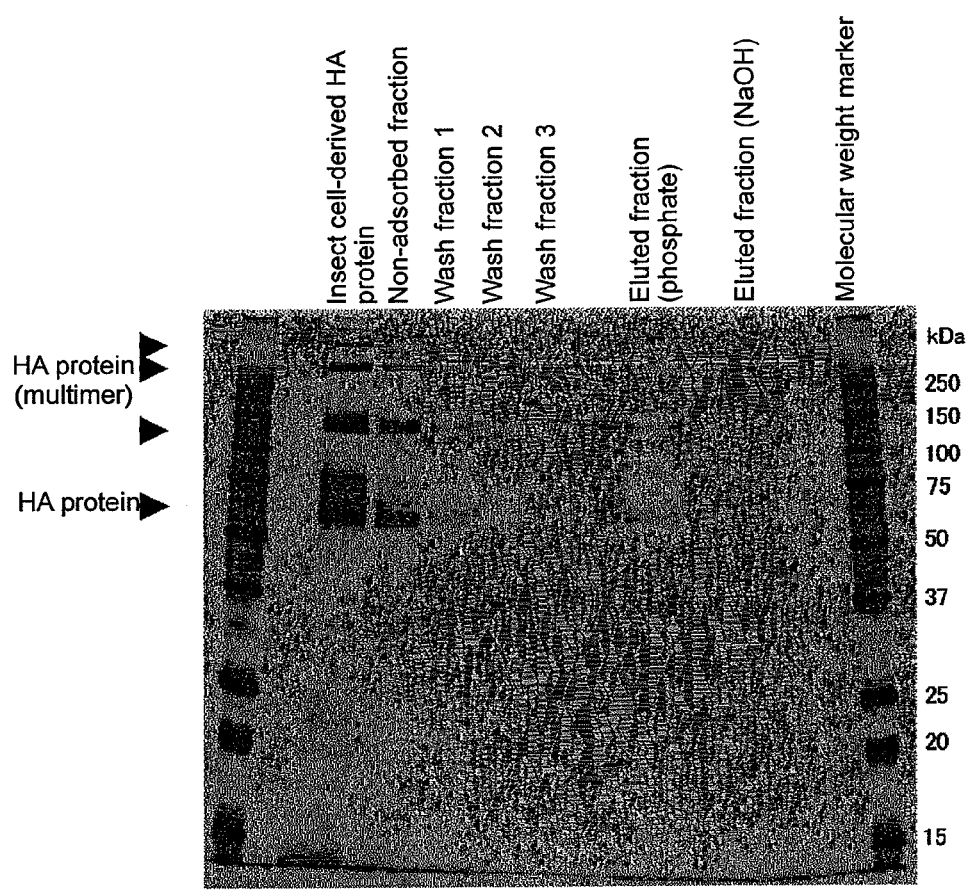
FIG. 14 is a diagram showing the result of SDS-PAGE (non-reducing, CBB staining) of each of the fractions obtained in Example 9.

The results of hydroxyapatite column chromatography and SDS-PAGE (non-reducing, silver staining) of each fraction are shown in FIG. 12. ConcB (%) in the figure has the same meaning as in Example 3. Further, the results of SDS-PAGE (non-reducing, silver staining) before and after the purification are shown in FIG. 13.

It was shown that, also with an influenza virus antigen derived from influenza virus of the H5N1 type, the purification can be carried out similarly to an influenza virus antigen derived from influenza virus of the H1N1 type.

Example 9

To 0.009 mL of HA protein of the H1 type produced by insect cells to which a gene that produces HA protein as an influenza virus antigen was incorporated (manufactured by Abcam plc., Cat. No. ab69741, 1.67 mg/mL, commercially available product), 0.072 mL of 20 mM phosphate buffered saline containing 1% Triton X-100 was added, and the resulting mixture was stirred, to provide the sample. On the membrane of a centrifugal filtration filter (Ultrafree-MC, manufactured by Millipore), 0.05 mL of a hydroxyapatite resin (Macro-Prep Ceramic Hydroxyapatite Type I 40 μm, manufactured by Bio-Rad) was placed, and 0.05 mL of the sample was added thereto, followed by centrifugation at 15,000×g for 30 seconds. The permeate was collected as the non-adsorbed fraction. To the hydroxyapatite resin remained on the upper side, 0.05 mL of 20 mM phosphate buffered saline was added, and the resulting mixture was stirred, followed by 3 times of the operation of centrifuging and washing in the same manner, after which the permeate was collected as the wash fraction. Subsequently, 0.05 mL of 250 mM phosphate buffer was added and the resulting mixture was stirred, followed by centrifuging the mixture in the same manner to carry out elution, after which the permeate was collected as the eluted fraction (phosphate). Further, 0.05 mL of 0.1 M NaOH solution was added and centrifugation was carried out in the same manner to carry out elution, after which the permeate was collected as the eluted fraction (NaOH). The obtained permeate was subjected to SDS-PAGE (non-reducing, CBB staining). The results are shown in FIG. 14.

Although the HA protein produced by insect cells to which a gene that produces HA protein as an influenza virus antigen was incorporated showed partial adsorption to the resin, the HA protein could be recovered as the non-adsorbed fraction and the wash fraction. Thus, it was shown that HA protein of the H1 type produced by recombinant insect cells can also be purified by recovering it as the non-adsorbed fraction and the wash fraction similarly to HA protein cultured with a chicken egg or animal cells.

INDUSTRIAL APPLICABILITY

As shown above, by the method of the present invention, an influenza virus antigen such as HA protein could be obtained by a simple operation, at high purity, and with a high recovery, from a sample such as culture liquid containing the influenza virus antigen together with various cultured impurities. Further, by the production method of the present invention, it is possible to economically obtain a highly safe and effective purified influenza virus antigen.

The invention claimed is:

1. A method for producing a purified influenza virus hemagglutinin (HA) antigen, said method comprising the steps of:
    treating a sample containing the influenza virus HA antigen with a surfactant;
    bringing said sample after the treatment into contact with hydroxyapatite in the presence of said surfactant under conditions where most of the HA antigen is not adsorbed by hydroxyapatite; and
    recovering a fraction not adsorbed by the hydroxyapatite, wherein said surfactant comprises at least one of an amphoteric surfactant 3-(3-cholamidepropyl)dimethylammonio-1-propanesulphonate, an nonionic surfactant polyoxyethyeneglycol p-t-octylphenyl ether and an anioni surfactant deoxycholic acid or a salt thereof.

2. The production method according to claim 1, wherein said sample containing an influenza virus antigen is an influenza virus grown by animal cell culture or chicken egg culture.

3. The production method according to claim 1, wherein said sample containing an influenza virus antigen is culture liquid of a recombinant cell produced by incorporating a gene for producing an influenza virus antigen to an animal cell or insect cell.

4. The production method according to any one of claims 1 to 3, wherein said surfactant treatment is carried out with a surfactant at a concentration of 0.05% to 20%.

5. The production method according to claim 1, wherein said surfactant comprises the amphoteric surfactant 3-(3-cholamidepropyl)dimethylammonio-1-propanesulphonate (CHAPS).

6. The production method according to claim 1, wherein said surfactant comprises the nonionic surfactant polyoxyethyleneglycol p-t-octylphenyl ether.

7. The production method according to claim 1, wherein said surfactant comprises the anionic surfactant deoxycholic acid or a salt thereof.

8. The production method according to claim 5, wherein said amphoteric surfactant is CHAPS and said surfactant treatment is carried out with a surfactant at a concentration of 0.5% to 20%.

9. The production method according to claim 6, wherein said nonionic surfactant is polyoxyethyleneglycol p-t-octylphenyl ether and said surfactant treatment is carried out with the surfactant at a concentration of 00.5% to 3%.

10. The production method according to claim 7, wherein said anionic surfactant is deoxycholic acid or a salt thereof and said surfactant treatment is carried out with the surfactant at a concentration of 1% to 20%.

11. The production method according to claim 1, wherein insoluble matter is removed from the sample after the surfactant treatment before the sample is brought into contact with hydroxyapatite.

12. The production method according to claim 1, wherein the sample after the surfactant treatment is brought into contact with hydroxyapatite under the condition of pH 6 to 10.

13. The production method according to claim 1, wherein, in said step of bringing the sample into contact with said surfactant and hydroxyapatite, hydroxyapatite is added to said treated sample in a batch-wise manner and the supernatant is then recovered as the fraction not adsorbed by hydroxyapatite.

14. The production method according to claim 1, wherein, in said step of bringing the sample into contact with hydroxyapatite, said treated sample is applied to a column filled with hydroxyapatite and the pass-through fraction from the column is recovered.

15. The production method according to claim 1, further comprising:
    adding an adjuvant and/or antiseptic to the recovered fraction not adsorbed by the hydroxyapatite to produce an influenza vaccine.

16. The production method according to claim 6, wherein said nonionic surfactant is polyoxyethyleneglycol p-t-octylphenyl ether polyoxyethyleneglycol (Triton X-100).

17. The production method according to claim 7, wherein said anionic surfactant is sodium deoxycholate (DOC).

* * * * *